United States Patent
Giebeler et al.

(10) Patent No.: US 9,568,365 B2
(45) Date of Patent: Feb. 14, 2017

(54) ATR INFRARED SPECTROMETER

(71) Applicants: PYREOS LTD., Edinburgh (GB); SPECTROLYTIC GMBH, Wernberg-Koeblitz (DE)

(72) Inventors: Carsten Giebeler, Edinburgh (GB); Benjamin Wiesent, Wernberg-Koeblitz (DE)

(*) Notice: Subject to any disclaimer, the term of this patent is extended or adjusted under 35 U.S.C. 154(b) by 0 days.

(21) Appl. No.: 15/186,172

(22) Filed: Jun. 17, 2016

(65) Prior Publication Data

US 2016/0299006 A1 Oct. 13, 2016

Related U.S. Application Data

(63) Continuation of application No. PCT/EP2014/075791, filed on Nov. 27, 2014.

(30) Foreign Application Priority Data

Dec. 17, 2013 (DE) .................. 10 2013 114 244

(51) Int. Cl.
*G01J 3/42* (2006.01)
*G01J 3/10* (2006.01)
(Continued)

(52) U.S. Cl.
CPC .................. *G01J 3/42* (2013.01); *G01J 3/108* (2013.01); *G01N 21/35* (2013.01); *G01N 21/552* (2013.01);
(Continued)

(58) Field of Classification Search
CPC .................. G01N 2201/12; G01N 2201/068; G01N 21/552; G01N 21/35; G01J 3/42; G01J 3/108
See application file for complete search history.

(56) References Cited

U.S. PATENT DOCUMENTS

| 4,975,581 A | 12/1990 | Robinson et al. |
| 2001/0030288 A1 | 10/2001 | Wilks, Jr. et al. |

(Continued)

FOREIGN PATENT DOCUMENTS

WO 2009/107988 A2 9/2009

OTHER PUBLICATIONS

International Search Report dated Feb. 18, 2015 of international application PCT/EP2014/075791 on which this application is based.

*Primary Examiner* — Mark R Gaworecki
(74) *Attorney, Agent, or Firm* — Ewers & Hasselmann PLLC

(57) ABSTRACT

An ATR infrared spectrometer for analyzing a chemical composition of a sample is provided including an elongated ATR crystal and having an entrance face, a longitudinal axis, a width, first and second longitudinal ends and an infrared light detector line with infrared-light-detecting regions. A first overall extent of all of the infrared-light-detecting regions corresponds to the width of ATR crystal. An infrared light emitter line has infrared-light-emitting regions and is arranged directly adjacent to the entrance face of the elongated ATR crystal. A sample is arranged adjacent to the ATR crystal between the infrared light emitter line and the infrared light detector line. Infrared light is emitted by the infrared light emitter line to directly enter said ATR crystal via said entrance face. The light is guided in the ATR crystal to said infrared light detector line thereby undergoing total internal reflection and thereby interacting with said sample.

15 Claims, 3 Drawing Sheets

(51) Int. Cl.
*G01N 21/552* (2014.01)
*G01N 21/35* (2014.01)

(52) U.S. Cl.
CPC ..... *G01N 2201/068* (2013.01); *G01N 2201/12* (2013.01)

(56) References Cited

U.S. PATENT DOCUMENTS

| | | |
|---|---|---|
| 2002/0079451 A1 | 6/2002 | Droessler et al. |
| 2009/0056434 A1 | 3/2009 | Csutak |
| 2010/0265509 A1 | 10/2010 | Jones et al. |

ATR INFRARED SPECTROMETER

CROSS REFERENCE TO RELATED APPLICATIONS

This application is a continuation application of international patent application PCT/EP2014/075791, filed Nov. 27, 2014, designating the United States and claiming priority from German application 10 2013 114 244.3, filed Dec. 17, 2013, and the entire content of both applications is incorporated herein by reference.

FIELD OF THE INVENTION

The invention relates to an ATR infrared spectrometer.

BACKGROUND OF THE INVENTION

An ATR infrared spectrometer is known for analyzing the chemical composition of a sample. The ATR infrared spectrometer (ATR: attenuated total reflection) has an elongated ATR crystal as an optical waveguide, in which infrared light is guided under total internal reflection, wherein approximately ten multiple reflections occur. Evanescent waves which interact with the sample arranged in the vicinity of the interface, for example on a sample stage, are formed behind the reflecting interface of the ATR crystal at the points of total internal reflection. By way of example, the material used for the ATR crystal is zinc sulfide or zinc selenide.

Arranged at the one longitudinal end of the ATR crystal is an infrared light source, by which the infrared light is coupleable into the ATR crystal. Arranged at the other longitudinal end, which is arranged distant from the one longitudinal end, is an infrared light sensor with a linearly variable wavelength filter, by which the spectrum of the infrared light decoupled from the ATR crystal is detectable. The zinc sulfide or the zinc selenide for the ATR crystal is used for wavelengths of the infrared light between 5.5 µm and 11.0 µm, wherein the linearly variable wavelength filter is tuned to this wavelength range in order to provide the corresponding spectral resolution using the infrared light sensor. By way of example, the infrared light sensor is a linear array made of a plurality of pyroelectric infrared light pixels. In order to obtain good illumination of the ATR crystal, the infrared light source is known to have a longitudinal extent which is at least as large as the longitudinal extent of the linear infrared light sensor array. Alternatively, use of a collimating lens between the infrared light source and the ATR crystal to focus the incident infrared light such that the linear infrared light sensor array is well-illuminated is known. Although this achieves a high spectral resolution of the ATR infrared spectrometer, the signal-to-noise ratio disadvantageously varies greatly over the relevant wavelength range of 5.5 µm to 11.0 µm.

FIG. 4 is a diagram which shows a curve of the signal-to-noise ratio of the ATR infrared spectrometer along the infrared light sensor array. The ordinate, denoted by reference numeral 16, specifies the signal-to-noise ratio, which is plotted over the abscissa 15, on which the positions of the individual infrared light pixels of the infrared light sensor array are shown in enumerated fashion. Infrared light with a wavelength of 5.5 µm is incident on the infrared light pixel with the position number 1 and infrared light with a wavelength of 11.0 µm is incident on the infrared light pixel with the position number 130. Incident on the infrared light pixels with the position numbers between 1 and 130 is infrared light with a wavelength between 5.5 µm and 11.0 µm, with the wavelength increasing linearly from the infrared light pixel with the position number 1 to the infrared light pixel with the position number 130. As can be seen in FIG. 4, the signal-to-noise ratio of the first 20 pixels is advantageously high. The signal-to-noise ratio is likewise still relatively high for the infrared light pixels with position numbers between 100 and 120. The signal-to-noise ratio is particularly low for the infrared light pixels with position numbers between 25 and 60. This uneven distribution of the signal-to-noise ratio over the infrared light pixels and hence over the wavelength range measured by the ATR infrared spectrometer is very disadvantageous, particularly if a signal-to-noise ratio which is as unchanging as possible over the whole wavelength measurement range is required for high accuracy of the analysis of the chemical composition of the sample.

SUMMARY OF THE INVENTION

It is an object of the invention to develop an ATR infrared spectrometer, by which a high measurement accuracy is achievable over the whole wavelength measurement range.

This object is achieved by providing an ATR infrared spectrometer for analyzing a chemical composition of a sample including: an elongated ATR crystal having an entrance face, a longitudinal axis, a width, a first longitudinal end, and a second longitudinal end; said entrance face being arranged at said first longitudinal end of said elongated ATR crystal; an infrared light detector line having a plurality of infrared-light-detecting regions and being arranged at said second longitudinal end of said elongated ATR crystal, wherein a first overall extent of all of the plurality of infrared-light-detecting regions of said infrared light detector line corresponds to said width of said elongated ATR crystal in a direction perpendicular to the longitudinal axis of said elongated ATR crystal; an infrared light emitter line having a plurality of infrared-light-emitting regions and being arranged directly adjacent to said entrance face of said elongated ATR crystal; said sample being arranged adjacent to said elongated ATR crystal between said infrared light emitter line and said infrared light detector line; said infrared light emitter line being configured to emit infrared light; said infrared light being emitted to directly enter said elongated ATR crystal via said entrance face and being guided in said elongated ATR crystal to said infrared light detector line thereby undergoing total internal reflection and interacting with said sample; and, said first overall extent being greater than a second overall extent of all of the plurality of infrared-light-emitting regions of said infrared light emitter line.

The ATR infrared spectrometer according to an aspect of the invention for analyzing the chemical composition of a sample has an elongated ATR crystal and an infrared light emitter line arranged directly adjacent to an entrance face of the ATR crystal arranged at one longitudinal end of the ATR crystal, and an infrared light detector line arranged at the other longitudinal end of the ATR crystal, wherein infrared light which is emitted by the infrared light emitter line directly enters into the ATR crystal via the entrance face and it is guided in the ATR crystal to the infrared light detector line under total internal reflection and with interaction with the sample which is arranged adjacent to the ATR crystal between the infrared light emitter line and the infrared light detector line, wherein the overall extent of all infrared-light-detecting regions of the infrared light detector line corresponds at most to the width of the ATR crystal in relation to the direction perpendicular to the longitudinal axis of the ATR crystal and it is greater than the overall extent of all infrared-light-emitting regions of the infrared light emitter line.

According to another aspect of the invention, the longitudinal axes of the infrared light emitter line and of the infrared light detector line each are perpendicular to the longitudinal axis of the ATR crystal. Preferably, in relation to the direction perpendicular to the longitudinal axis of the ATR crystal, the infrared light emitter line, with its overall extent of all infrared-light-emitting regions, is arranged within the overall extent of all infrared-light-detecting regions of the infrared light detector line, which overall extent of all infrared-light-detecting regions of the infrared light detector line, in relation to the direction perpendicular to the longitudinal axis of the ATR crystal, is arranged within the extent of the width of the ATR crystal. Furthermore, in a direction perpendicular to the longitudinal axis of the ATR crystal, the overall extent of all infrared-light-emitting regions of the infrared light emitter line preferably corresponds to an extend between 15% and 95% of the overall extent of all infrared-light-detecting regions of the infrared light detector line.

Preferably, the infrared light emitter line has infrared light pixels arranged in a row along the longitudinal axis of the infrared light emitter line. The infrared light pixels preferably each corresponds to one of the infrared-light-emitting regions which are directly adjacent to one another in the direction perpendicular to the longitudinal axis of the ATR crystal. Alternatively, the infrared light pixels each correspond to one of the infrared-light-emitting regions, wherein the number of infrared light pixels and the overall extent of their infrared-light-emitting regions are matched to one another in the direction perpendicular to the longitudinal axis of the ATR crystal in such a way that the coverage of the infrared-light-emitting regions of the infrared light pixels corresponds to at least 25% of the overall extent of all infrared-light-emitting regions of the infrared light emitter line.

According to yet another aspect of the invention, the infrared-light-emitting regions of the infrared light pixels are rectangular in each case. One of the diagonals of the infrared-light-emitting regions of the infrared light pixels is preferably perpendicular to the longitudinal axis of the ATR crystal. Alternatively, one of the side edges of the infrared-light-emitting regions of the infrared light pixels is perpendicular to the longitudinal axis of the ATR crystal.

The infrared light detector line according to a further aspect of the invention has a linearly variable wavelength filter, the light transmissivity of which varies perpendicular to the longitudinal axis of the ATR crystal. According to yet another aspect of the invention, the ATR crystal is made of zinc sulfide or zinc selenide and the spectral range of the wavelength filter is between 5.5 µm and 11.0 µm. The ATR infrared spectrometer is operable with infrared light of all wavelengths at which the ATR crystal is transparent. The spectral range of the wavelength filter includes the wavelength range within which the ATR crystal is transparent, or sections thereof.

Furthermore, the infrared light detector line preferably has a plurality of pyroelectric infrared light sensor pixels. It is preferable for the pyroelectric infrared light sensor pixels to have a thin film of lead zirconate titanate for detecting infrared light. According to another aspect of the invention, the thin film is thinner than the wavelength of the infrared light to be detected.

According to a further aspect of the invention, as a result of the overall extent of all infrared-light-detecting regions of the infrared light detector line corresponding at most to the width of the ATR crystal in relation to the direction perpendicular to the longitudinal axis of the ATR crystal and as a result of this being greater than the overall extent of all infrared-light-emitting regions of the infrared light emitter line, the signal-to-noise ratio of the ATR infrared spectrometer according to an aspect of the invention is uniformly high over the whole range of wavelengths of the spectrum detectable by the infrared light detector line. By way of example, according to a further aspect of the invention, drops in the signal-to-noise ratio of the ATR infrared spectrometer, as are known from the prior art, do not occur. The signal-to-noise ratio of the ATR infrared spectrometer according to an aspect of the invention is uniformly high over the whole wavelength range thereof, and so a high measurement accuracy is obtained.

As a result of the dimensioning, the overall extents of all infrared-light-emitting and infrared-light-detecting regions, the light cone of the infrared light which enters into the ATR crystal via the entrance face is such that the equalization of the signal-to-noise ratio of the ATR infrared spectrometer is obtained at a high level. The overall extent of all infrared-light-emitting regions can lie between two 250 µm and 1000 µm, wherein, for example, ten of the infrared light pixels are provided for the infrared light emitter line. Furthermore, the overall extent of all infrared-light-emitting regions can lie between 1000 µm and 3000 µm, wherein the infrared light emitter line has two of the infrared light pixels.

The invention is based on the observation that additional interference effects occur in the thin layer when the infrared light to be detected is incident in a slightly oblique manner on the infrared light detector line. It was established empirically that these interference effects cause the equalization of the signal-to-noise ratio which is obtained according to the various aspects of the invention. These interference effects are achieved by virtue of the overall extent of all infrared-light-detecting regions of the infrared light detector line corresponding at most to the width of the ATR crystal and being greater than the overall extent of all infrared-light-emitting regions of the infrared light emitter line. The interference effects in the thin layer do not occur in an ATR infrared spectrometer in which the dimensioning according to an aspect of the invention of the infrared-light-emitting and infrared-light-detecting regions has not been provided, and so this ATR infrared spectrometer has a strongly non-uniform distribution of the signal-to-noise ratio over the wavelength.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
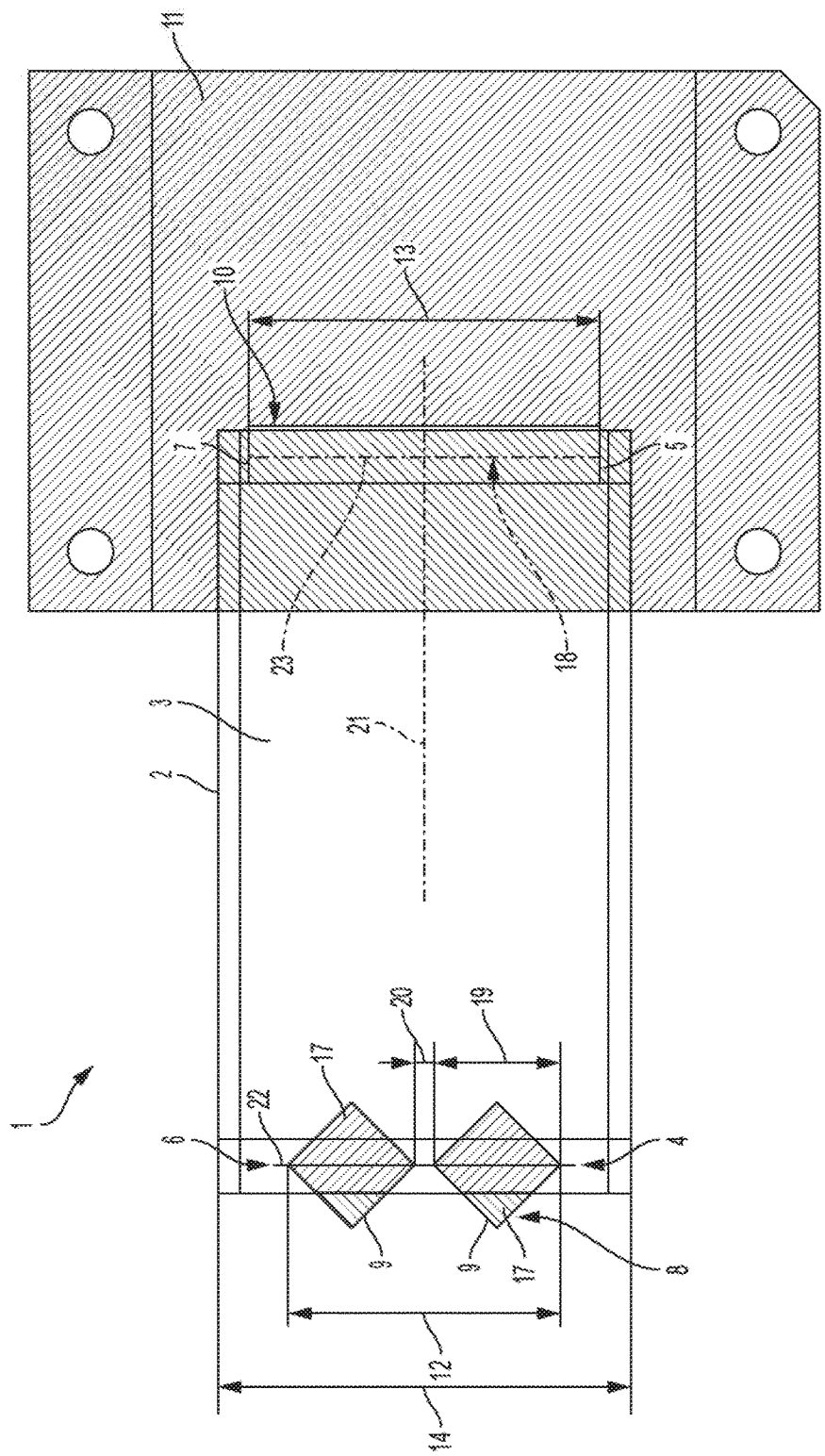
FIG. 1 is a plan view of an ATR infrared spectrometer according to an exemplary embodiment of the invention.
Figure 2:
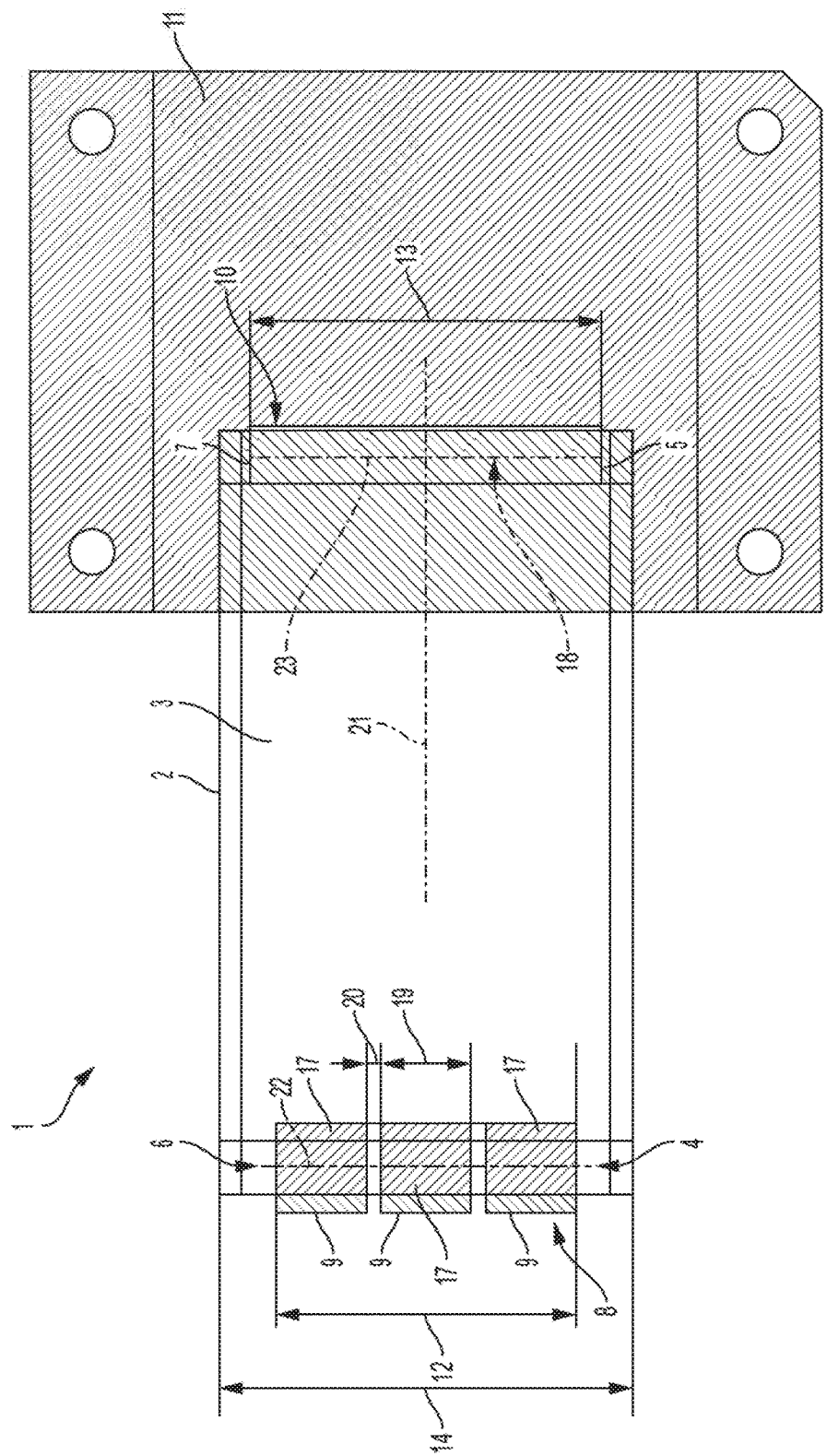
FIG. 2 is a plan view of an ATR infrared spectrometer according to another exemplary embodiment of the invention.

As shown in FIGS. 1 and 2, the ATR infrared spectrometer 1 according to an exemplary embodiment of the invention has an elongated ATR crystal 2 with a longitudinal axis 21. In the plan view, the ATR crystal 2 has a rectangular base, wherein one of the two rectangular surfaces, in particular the upper surface, is a sample stage 3. A sample, the chemical composition of which can be analyzed by the ATR infrared spectrometer 1, should be arranged on the sample stage 3. A first entrance face 4 of the ATR crystal 2 is provided at one of the end sides of the ATR crystal and an exit face 5 of the ATR crystal 2 is provided at the other end side arranged at a distance from the one end side, wherein infrared light enters into the ATR crystal 2 through the entrance face 4 and emerges from the ATR crystal 2 from the exit face 5. A first reflection face 6 is provided at the ATR crystal 2 adjacent to the entrance face 4 and a second reflection face 7 is provided at the exit face 5, wherein the reflection faces 6, 7 are arranged in such a way that infrared light, which enters into the ATR crystal 2 via the entrance face 4, undergoes multiple total internal reflections in the ATR crystal 2 and then emerges from the ATR crystal 2 via the exit face 5. The entrance face 4 and the exit face 5 are arranged parallel to the sample stage 3, whereas the reflection faces 6, 7 are arranged at an angle with respect to the sample face 3.

An infrared light emitter line 8, which is formed by the infrared light pixel 9, is arranged directly adjacent to the entrance face 4. The exemplary embodiment shown in FIG. 1 has two infrared light pixels 9 and the exemplary embodiment shown in FIG. 2 has three infrared light pixels 9. The infrared light pixels are configured to emit infrared light, the wavelength range of which has a range between 5.5 µm and 11.0 µm. The ATR crystal 2 is made of zinc sulfide or zinc selenide. The infrared light emitted by the infrared light pixel 9 is coupled into the ATR crystal 2 via the entrance face 5, it undergoes total internal reflection at the first reflection face 6 and it is then guided within the ATR crystal 2 by way of a multiplicity of total internal reflections at the sample stage 3 and at the surface of the ATR crystal 2 arranged at a distance from the sample stage 3 to the second reflection face 7, at which the infrared light is reflected toward the exit face 5, and there it is decoupled from the ATR crystal 2. The infrared light emitted by the infrared light pixels 9 is directly incident on the entrance face 4, since, for example, neither a concave mirror nor a collimator lens is provided at the infrared light pixel 9 for the purposes of focusing the infrared light. The infrared light emitter line 8 has a longitudinal axis 22, which extends perpendicular to the longitudinal axis 21 of the ATR crystal 2.

An infrared light detector line 10 is provided at the ATR crystal 2 at a distance from the infrared light emitter line 8 and directly arranged immediately at the exit face 5. The infrared light detector line 10 has a longitudinal axis 23, which is parallel to the longitudinal axis 22 of the infrared light emitter line 8 and perpendicular to the longitudinal axis 21 of the ATR crystal 2. The infrared light detector line 10 is formed by a plurality of pyroelectric infrared light sensor pixels, which each have a thin layer made of lead zirconate titanate. Arranged between the infrared light detector line 10 and the exit face 5 is a linearly variable wavelength filter, the spectral range of which is 5.5 µm to 11.0 µm. Hence, the one infrared light sensor pixel, which is arranged directly adjacent to the one end of the linearly variable wavelength filter, the light passage of which lies at 5.5 µm, is merely impinged upon by infrared light with precisely this wavelength. Analogously, only infrared light with a wavelength of 11.0 µm impinges on the infrared light sensor pixel arranged at a distance therefrom. Infrared light with a wavelength between 5.5 µm and 11.0 µm impinges between these two outer infrared light sensor pixels, with the spectrum curve of the wavelength filter being linear. The infrared light detector line 10 has 130 infrared light sensor pixels, wherein the one outer infrared light pixel with the position number 1 lies at that end of the wavelength filter at which infrared light with 5.5 µm is passed, and the other outer infrared sensor pixel with the number 130 lies at the other end of the wavelength filter, at which infrared light with a wavelength of 11.0 µm is passed.

Provided at the infrared light detector line 10 is an evaluation platform 11 of the ATR infrared spectrometer 2, by which a sample arranged on the sample stage 3 is evaluable by way of appropriate electronics for the purposes of a spectral analysis.

The thin layers of the infrared sensor pixels made of lead zirconate titanate are thinner than the wavelength of the infrared light incident thereon, that is, the infrared light passed thereto by way of the linearly variable wavelength filter. In the exemplary embodiments shown in FIGS. 1 and 2, the thickness of the thin layers made of lead zirconate titanate is selected to be smaller than the smallest wavelength of the infrared light which passes the wavelength filter. That is, the thin layers of the infrared light sensor pixels are embodied to be thinner than 5.5 µm in the shown exemplary embodiments.

In accordance with the exemplary embodiments shown in FIGS. 1 and 2, the infrared light pixels 9 each have a rectangular emission face 17, wherein the emission faces 17 of the infrared light pixels 9 have embodiments with the same dimensions. The infrared light pixels 9 are arranged along the longitudinal axis 22 of the infrared light emitter line 8, wherein the center points of the rectangular emission faces lie on the longitudinal axis 22 of the infrared light emitter line 8.

The exemplary embodiment shown in FIG. 1 has the two infrared light pixels 9, wherein one diagonal of the emission faces 17 of the infrared light pixels 9 lies on the longitudinal axis 22 of the infrared light emitter line 8 in each case. As result, the width 19 of the infrared light emission from the emission face 17 is defined by the length of the diagonal for each infrared light pixel 9. In the exemplary embodiment shown in FIG. 2, the diagonals of the emission faces 17 of the three infrared light pixels 9 cross the longitudinal axis 22 of the infrared light emitter line 8 at an angle of 45°, and so the widths 19 of the infrared light emission of the emission faces 17 are defined by the side length of the emission faces 19 in each case. In the exemplary embodiment of FIG. 1 and in the exemplary embodiment of FIG. 2, a spacing 20 is respectively provided between the infrared light pixels 9. The overall length 12 of the infrared light emission of the emission faces 17 of the infrared light pixels 9 of the infrared light emitter line 8 is defined by the two extreme extents of the infrared light pixels 9 of the infrared light emitter line 8, wherein the spacing 20 of the infrared light pixels 9 in accordance with FIG. 1 and the spacings 20 of the infrared light pixels 9 in accordance with FIG. 2 are arranged within the overall length 12 of the infrared light emission.

The infrared light detector line 10 has a detection face 18 which extends along the longitudinal axis 23 of the infrared light detector line 10 and along which the infrared sensor pixels for detecting infrared light are arranged. The extent of the emission face 17 along the longitudinal axis 23 of the infrared light detection line 10 provides the overall length 13 of the infrared light detection, wherein the overall length of the infrared light emission 12 is less than the overall length 13 of the infrared light detection. Furthermore, the ATR crystal 2 with the width 14 thereof covers the overall length 13 of the infrared light detection and therefore the overall length 12 of the infrared light emission. The row of emission faces 17 and the row of detection faces 18 are in each case arranged symmetrically with respect to the longitudinal axis 21 of the ATR crystal 2.

The side lengths of the emission faces 17 in accordance with the exemplary embodiments shown in FIGS. 1 and 2 are 2 mm, wherein the spacing 20 between the infrared light pixels 9 is 11.03 mm in the exemplary embodiment shown in FIG. 1 and the spacings 20 are 12.30 mm in the embodiment shown in FIG. 2.

Figure 3:
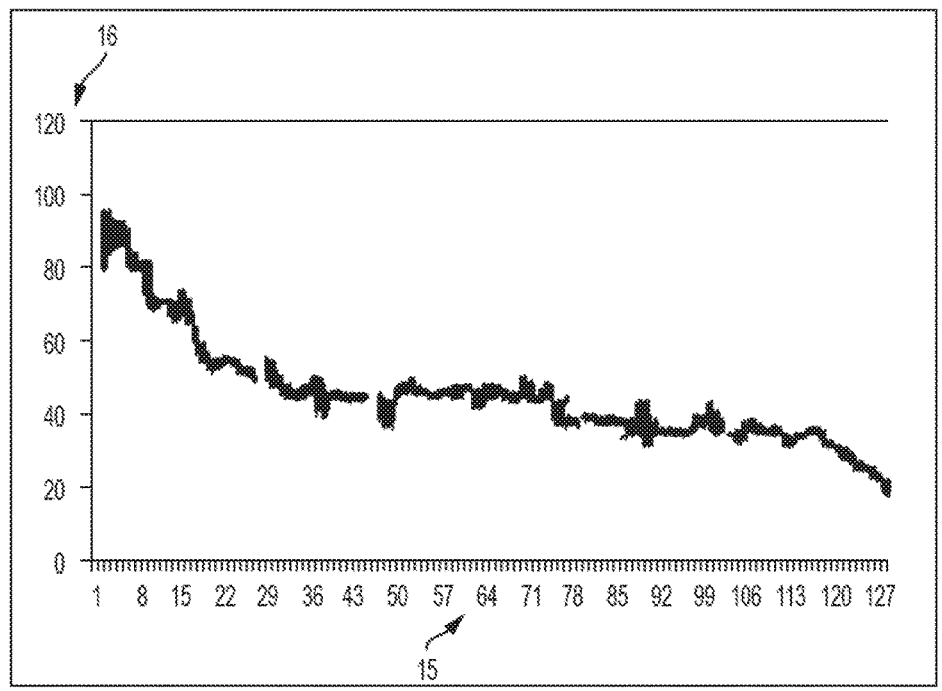
FIG. 3 is a diagram showing a curve of a signal-to-noise ratio of a wavelength spectrum of the ATR infrared spectrometer according to an exemplary embodiment of the invention; and, FIG. 4 is a diagram showing a curve of the signal-to-noise ratio of a conventional ATR infrared spectrometer.
Figure 4:
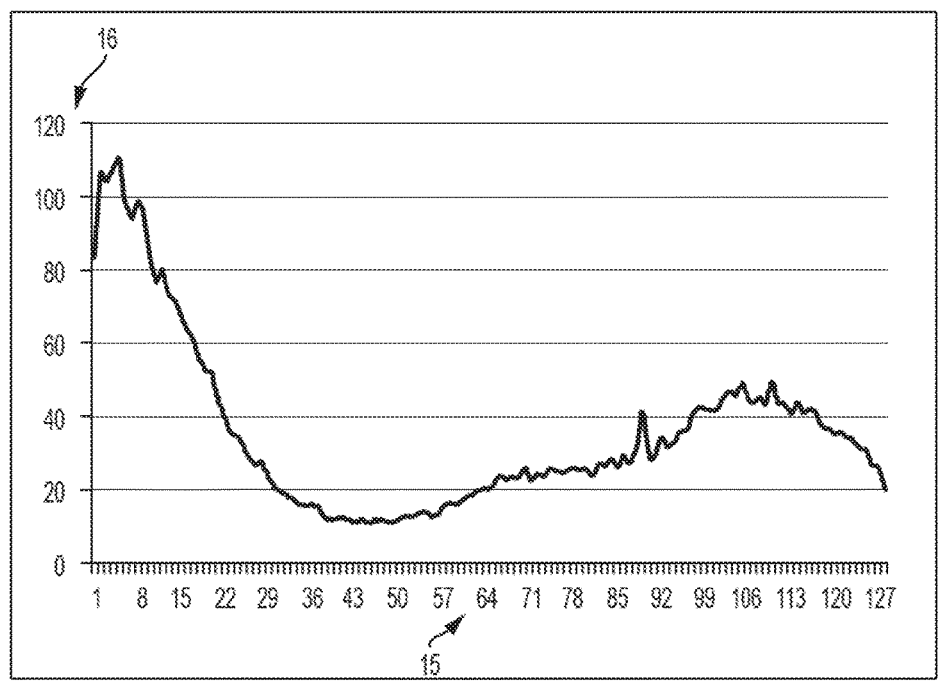

FIGS. 3 and 4 each are diagrams which show the signal-to-noise ratio 16 along the infrared light detector line 10, wherein the abscissa 15 specifies the positions of the infrared light sensor pixels in the infrared light detector line 10 with position numbers from 1 to 130. Infrared light with a wavelength of 5.5 µm is incident on the infrared light sensor pixel with the number 1 and infrared light with a wavelength of 11.0 µm is incident on the infrared light pixel with the position number 130. Infrared light, the wavelength of which lies between 5.5 µm and 11.0 µm, is incident on the infrared light sensor pixels lying between the infrared light sensor pixel with the position number 1 and the infrared light sensor pixel with the position number 127, wherein the wavelength increases linearly from the infrared light sensor pixel with the position number 1 to the infrared light sensor pixel with the position number 127.

The diagram shown in FIG. 3 plots a curve of the signal-to-noise ratio 16 of the exemplary embodiments shown in FIGS. 1 and 2. It is possible to identify that the signal-to-noise ratio is highest for those infrared light sensor pixels with the lowest position numbers and it is lowest for those infrared light sensor pixels with the highest position numbers. This decrease is monotonic and comparatively uniform.

The diagram depicted in FIG. 4 shows a curve of the signal-to-noise ratio 16 along an infrared light detector line of an ATR infrared spectrometer, in which an infrared light emitter line has an infrared light emission region, the overall length of which is greater than the overall length of the infrared detection region of the infrared light detector line. It is possible to identify that the curve of the signal-to-noise ratio 16 is comparable to the diagram depicted in FIG. 3 in both edge regions, but it is possible to identify a significant drop in the signal-to-noise ratio in the case of infrared light sensor pixels with position numbers between 20 and 60. In this region, the signal-to-noise ratio is even lower than for those infrared light sensor pixels with the highest position numbers. This non-monotonic curve of the signal-to-noise ratio 16 and the considerable drop in the signal-to-noise ratio for infrared light pixels with middling position numbers leads to a significant measurement inaccuracy of this known ATR infrared spectrometer. By contrast, as shown in FIG. 3, the curve of the signal-to-noise ratio 16 along the infrared light detection line 10 is monotonic and uniform, as result of which the ATR infrared spectrometer 1 according to the invention has a high measurement accuracy.

It is understood that the foregoing description is that of the preferred embodiments of the invention and that various changes and modifications may be made thereto without departing from the spirit and scope of the invention as defined in the appended claims.

LIST OF REFERENCE NUMERALS

1 ATR infrared spectrometer
2 ATR crystal
3 Sample stage
4 Entrance face
5 Exit face
6 First reflection face
7 Second reflection face
8 Infrared light emitter line
9 Infrared light pixel
10 Infrared light detector line
11 Evaluation platform
12 Overall length of the infrared light emission
13 Overall length of the infrared light detection
14 Width of the ATR crystal
15 Abscissa: Position numbers of the infrared sensor pixels of the infrared light detector line
16 Ordinate: Signal-to-noise ratio
17 Emission face
18 Detection face
19 Width of the infrared light emission of the emission face
20 Spacing of the infrared light pixel
21 Longitudinal axis of the ATR crystal
22 Longitudinal axis of the infrared light emitter line
23 Longitudinal axis of the infrared light detector line

What is claimed is:

1. An ATR infrared spectrometer for analyzing a chemical composition of a sample, the ATR infrared spectrometer comprising:
   an elongated ATR crystal having an entrance face, a longitudinal axis, a width, a first longitudinal end, and a second longitudinal end;
   said entrance face being arranged at said first longitudinal end of said elongated ATR crystal;
   an infrared light detector line having a plurality of infrared-light-detecting regions and being arranged at said second longitudinal end of said elongated ATR crystal, wherein a first overall extent of all of the plurality of infrared-light-detecting regions of said infrared light detector line corresponds to said width of said elongated ATR crystal in a direction perpendicular to the longitudinal axis of said elongated ATR crystal;
   an infrared light emitter line having a plurality of infrared-light-emitting regions and being arranged directly adjacent to said entrance face of said elongated ATR crystal;
   said sample being arranged adjacent to said elongated ATR crystal between said infrared light emitter line and said infrared light detector line;
   said infrared light emitter line being configured to emit infrared light;
   said infrared light being emitted to directly enter said elongated ATR crystal via said entrance face and being guided in said elongated ATR crystal to said infrared light detector line thereby undergoing total internal reflection and interacting with said sample; and,
   said first overall extent being greater than a second overall extent of all of the plurality of infrared-light-emitting regions of said infrared light emitter line.

2. The ATR infrared spectrometer of claim 1, said infrared light emitter line having a first longitudinal axis and said infrared light detector line having a second longitudinal axis, wherein each of said first and second longitudinal axes is arranged perpendicular to said longitudinal axis of said elongated ATR crystal.

3. The ATR infrared spectrometer of claim 2, wherein the infrared light emitter line includes infrared light pixels arranged in a row along the first longitudinal axis of said infrared light emitter line.

4. The ATR infrared spectrometer of claim 3, wherein each of the infrared light pixels represents one of the plurality of infrared-light-emitting regions which are arranged directly adjacent to one another in the direction perpendicular to the longitudinal axis of the elongated ATR crystal.

5. The ATR infrared spectrometer as claimed in claim 3, wherein:
each of the infrared light pixels corresponds to at least one of the plurality of infrared-light-emitting regions, and
a number of the infrared light pixels is matched with the second overall extent of the plurality of infrared-light-emitting regions in the direction perpendicular to the longitudinal axis of the elongated ATR crystal so that a coverage of the infrared-light-emitting regions of the infrared light pixels corresponds to at least 25% of the second overall extent of all of the plurality of infrared-light-emitting regions of said infrared light emitter line.

6. The ATR infrared spectrometer of claim 3, wherein the infrared-light-emitting regions of said infrared light pixels have a rectangular shape.

7. The ATR infrared spectrometer of claim 6, wherein a diagonal of the infrared-light-emitting regions of the infrared light pixels is arranged perpendicular to the longitudinal axis of the elongated ATR crystal.

8. The ATR infrared spectrometer of claim 6, wherein a side edge of the infrared-light-emitting regions of the infrared light pixels is arranged perpendicular to the longitudinal axis of the elongated ATR crystal.

9. The ATR infrared spectrometer of claim 1, wherein, in the direction perpendicular to the longitudinal axis of the elongated ATR crystal, said infrared light emitter line with said second overall extent of all of the plurality of infrared-light-emitting regions is arranged within the first overall extent of all of the plurality of infrared-light-detecting regions of said infrared light detector line which is, with the first overall extent of all infrared-light-detecting regions, arranged within the width of said elongated ATR crystal.

10. The ATR infrared spectrometer of claim 1, wherein, in the direction perpendicular to the longitudinal axis of the elongated ATR crystal, the second overall extent of all of the plurality of infrared-light-emitting regions of the infrared light emitter line corresponds to an extent between 15% and 95% of the first overall extent of all of the plurality of infrared-light-detecting regions of the infrared light detector line.

11. The ATR infrared spectrometer of claim 1, wherein:
said infrared light detector line includes a linearly variable wavelength filter, and
a light transmissivity of the linearly variable wavelength filter varies in the direction perpendicular to the longitudinal axis of the elongated ATR crystal.

12. The ATR infrared spectrometer of claim 11, wherein:
the elongated ATR crystal is made of zinc sulfide or zinc selenide, and
a spectral range of the linearly variable wavelength filter is between 5.5 μm and 11.0 μm.

13. The ATR infrared spectrometer of claim 1, wherein said infrared light detector line includes a plurality of pyroelectric infrared light sensor pixels.

14. The ATR infrared spectrometer of claim 13, wherein the pyroelectric infrared light sensor pixels include a thin film of lead zirconate titanate for detecting infrared light.

15. The ATR infrared spectrometer of claim 14, wherein the thin film is thinner than a wavelength of the infrared light to be detected.

* * * * *

UNITED STATES PATENT AND TRADEMARK OFFICE
CERTIFICATE OF CORRECTION

PATENT NO. : 9,568,365 B2
APPLICATION NO. : 15/186172
DATED : February 14, 2017
INVENTOR(S) : Carsten Giebeler et al.

It is certified that error appears in the above-identified patent and that said Letters Patent is hereby corrected as shown below:

On the Title Page

Please insert:
--(73) Assignee: PYREOS LTD., Edinburgh (GB)
     SPECTROLYTIC GMBH, Wernberg-Koblitz (DE)--

Signed and Sealed this
Fifth Day of February, 2019

Andrei Iancu
*Director of the United States Patent and Trademark Office*